United States Patent [19]
von der Saal et al.

[11] Patent Number: 5,135,949
[45] Date of Patent: Aug. 4, 1992

[54] PHARMACEUTICAL COMPOSITIONS CONTAINING PHENYLAMIDES

[75] Inventors: Wolfgang von der Saal, Weinheim; Alfred Mertens, Schriesheim; Harald Zilch, Mannheim; Erwin Boehm, Ladenburg, all of Fed. Rep. of Germany

[73] Assignee: Boehringer Mannheim GmbH, Mannheim, Fed. Rep. of Germany

[21] Appl. No.: 402,185

[22] Filed: Sep. 5, 1989

[30] Foreign Application Priority Data

Sep. 3, 1988 [DE] Fed. Rep. of Germany .... 3830054.0

[51] Int. Cl.$^5$ .................. A61K 31/275; A61K 31/165
[52] U.S. Cl. ..................................... 514/520; 514/617; 514/618; 514/619; 514/620; 514/822
[58] Field of Search ............... 514/617, 619, 620, 520, 514/618, 822

[56] References Cited

U.S. PATENT DOCUMENTS 3,936,479  2/1976  Avar et al. ........................... 260/404
4,008,274  2/1977  Sawatari et al. ..................... 564/179

FOREIGN PATENT DOCUMENTS 0008391  3/1980  European Pat. Off. .
0118752  9/1984  European Pat. Off. .
0148725  7/1985  European Pat. Off. .
0170105  2/1986  European Pat. Off. .
0268267  5/1988  European Pat. Off. .
2376858  1/1987  France .
2038814  7/1980  United Kingdom .
2164648  3/1986  United Kingdom .

OTHER PUBLICATIONS

Japanese Application 56–29552 (1981) (Abstract only).
Chemical Abstracts 73:76840b (1970).
Chemical Abstracts, vol. 94, Nr. 22881f. Jan. 1981.
Patent Abstracts of Japan, vol. 4, Nr. 166, Nov. 1980.
Patent Abstracts of Japan, vol. 4, Nr. 159, Nov. 1980.
Glusa, E. et al. Chem. Abstracts 82(1):100a (1975).
In: Thromb. Dath Haemorrh. 3(1): 172–8 (1974).
Yamanouchi Chem. Abstracts 100: 22662c (1984).

Primary Examiner—Richard L. Raymond
Assistant Examiner—Gary E. Hollinden
Attorney, Agent, or Firm—Nikaido, Marmelstein, Muray & Oram

[57] ABSTRACT

Pharmaceutical compositions for inhibiting the aggregation of erthyrocytes or thrombocytes which include phenylamides which conform to the formula:

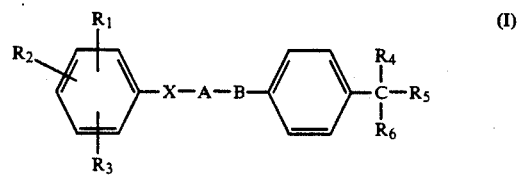

with $R_{1-6}$, X, A and B being as defined. Processes for the preparation of novel phenylamides coming within the above formula are also discussed.

18 Claims, No Drawings

PHARMACEUTICAL COMPOSITIONS CONTAINING PHENYLAMIDES

The present invention is concerned with pharmaceutical compositions containing phenylamides, some of which are new, and with processes for the preparation of the new phenylamides.

Thus according to one aspect of the present invention, there are provided pharmaceutical compositions containing, in addition to conventional carrier and adjuvant materials, at least one phenylamide of the general formula:

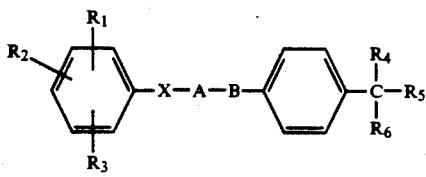

wherein $R_1$, $R_2$ and $R_3$ are the same or different and each represents a hydrogen atom, alkyl, alkenyl, alkynyl, cycloalkyl, cycloalkenyl, phenyl, halogen, nitro, amino, formyl, hydroxyl, mercapto or cyano, or a hydroxyl group substituted by alkyl, alkenyl, alkynyl, cycloalkyl, cycloalkenyl, phenyl, benzyl, pyridinyl, alkylsulphonyl, trifluoromethylsulphonyl, alkylcarbonyl, cyanoalkyl, hydroxyalkyl, dialkylaminoalkyl, aminocarbonylalkyl, dialkylaminocarbonylalkyl, N-cycloalkyl-N-alkylaminocarbonylalkyl, carboxyalkyl, alkoxycarbonylalkyl or alkoxyalkyl, or an amino group substituted once or twice by alkylsulphonyl, trifluoromethylsulphonyl, alkylcarbonyl, formyl, aminocarbonyl, alkylaminocarbonyl or alkyl, or a carbonyl group substituted by hydroxyl, alkyl, alkoxy, amino, alkylamino or dialkylamino, or a sulphonyl group substituted by amino, alkylamino, piperidino, morpholino or thiomorpholino or is an alkylthio, alkylsulphinyl or alkylsulphonyl radical or wherein two substituents $R_2$ and $R_3$ which are ortho to one another, together with the carbon atoms to which they are attached, form a five-or six-membered ring, X is a valency bond or an alkylene radical or, when A is a carbonyl group —CO—, is also an alkenylene radical, A and B are different and are the carbonyl group —CO— or the imino group —NH—, $R_4$ is methyl, cyano, aminocarbonyl or aminomethyl, $R_5$ is a hydrogen atom or an alkyl radical and $R_6$ is an alkyl or cycloalkyl radical or $R_5$ and $R_6$, together with the carbon atom to which they are attached, form a cycloalkyl ring, the optically-active forms thereof, the tautomers thereof and the physiologically compatible salts thereof with inorganic and organic acids.

The present invention also provides new phenylamides, processes for the preparation thereof and the use thereof for the preparation of pharmaceutical compositions and especially of pharmaceutical compositions with an erythrocyte aggregation-inhibiting action.

If the compounds of general formula (I) contain a centre of asymmetry or an asymmetric plane, the present invention also includes the optically-active forms and racemic mixtures of these compounds.

Pharmaceutical compositions which contain compounds (I) display valuable pharmacological properties and, in particular, they inhibit the aggregation of erythrocytes and can thus be used for the treatment of diseases in the pathogenesis of which erythrocyte aggregation plays an important part, for example peripheral, coronary and cerebral circulatory disturbances, states of shock and the like. Furthermore, the compounds influence the thrombocyte function, increase the power of the heart and have a blood pressure-lowering action.

Some compounds of structural similarity which are not included within the scope of the present invention are already known as medicaments.

Thus, for example Swiss Patent Specification No. 609,558 and U.S. patent Application No. 398,522 (18th Sep., 1973; L. Givaudan et Cie.) describe the anti-bacterial action of compounds in which $R_4$, $R_5$ and $R_6$ are methyl radicals, B is a carbonyl group, A is an imino group —NH—, X is a valency bond and one of the substituents $R_1$, $R_2$ and $R_3$ is a trifluoromethyl radical in the meta-position of the phenyl ring and the other two are hydrogen or halogen atoms or trifluoromethyl radicals and especially the compounds 4-(1,1-dimethylethyl)-N-[3-trifluoromethyl)-phenyl]-benzamide and N-[4-chloro-3-trifluoromethyl)-phenyl]-4-(1,1-dimethylethyl)-benzamide.

U.S. Pat. No. 4,160,097 (Jul. 3rd, 1979 Westwood pharmaceuticals) describes the inflammation-inhibiting action of 4-(1,1-dimethylethyl)-N-[2-(1H-imidazol-1-yl)-phenyl]-benzamide.

Of the following compounds which are within the scope of the present invention, the synthesis thereof has already been described but not the use thereof as medicaments:

N-[2-(aminocarbonyl)-phenyl]-4-(1,1-dimethylethyl)-benzamide in U.S. patent application No. 450,870 (16.3.76; FMC Corp.);

4-(1,1-dimethylethyl)-N-phenylbenzamide in S. Ito et al., Nippon Noyaku Gakkashi, 10, 697;

N-(2,6-dihydroxyphenyl)-4-(1,1-dimethylethyl)-benzamide in British Patent Specification No. 2,018,453 (14.10.1979, Eastman Kodak);

4-(1,1-dimethylethyl)-N-[2-(1-methylethoxy)-phenyl]-benzamide in Japanese Patent Application No. 77/496 (6.1.1977; Kumiai Chemical Industry Co);

4-(1,1-dimethylethyl)-N-[3-(1,1-dimethylethyl)-4-(octyloxy)-phenyl]-benzamide in Japanese Patent Application No. 55/6321 (17.1.1980; Konishiroku Photo Industry Co.);

methyl 2-[[4-(1,1-dimethylethyl)-benzoyl]-amino]-benzoate in K. Osann et al., Agric. Biol. Chem., 44, 2143;

N-(2,3-dichlorophenyl)-4-(1,1-dimethylethyl)-benzamide in Japanese Patent Application No. 55/76851 (5.10.1978, Hodogaya Chemical Co);

4-(1,1-dimethylethyl)-N-[4-(1-methylethoxy)-phenyl]-benzamide in Japanese Patent Application No. 55/108846 (21.6.1980; Humiai Chemical Ind.);

4-(1,1-dimethylethyl)-N-[4-(1,1-dimethylethyl)-phenyl]-benzamide in F. Bell, J. A. Gibson, R. D. Wilson, J. Chem. Soc., 1956, 2335;

4-(1,1-dimethylethyl)-N-(3-ethyl-4-hydroxyphenyl)-benzamide in South African Patent Application No. 68/5360 (19.2.1970; ICI);

4-(1,1-dimethylethyl)-N-[3-(1,1-dimethylethyl)-4-hydroxy-5-methylphenyl]-benzamide in U.S. Pat. No. 4,025,487 (24.5.1977; Ciba-Geigy); 4-(1,1-dimethylethyl)-N-(2-hydroxy-4-nitrophenyl)-benzamide, N-(4-amino-2-hydroxyphenyl)-4-(1,1-dimethylethyl)-benzamide and 4-(1,1-dimethylethyl)-N-[2-hydroxy-4-[(2-methyl-1-oxo-2-propenyl)-amino]-phenyl]-benzamide in Federal Republic of Germany Patent Application No. 2156480 (6.6.1972; Agfa);

N-(5-chloro-2-hydroxy-4-nitrophenyl)-4-(1,1-dimethylethyl)-benzamide and N-(4-amino-5-chloro-2-hydroxyphenyl)-4-(1,1-dimethylethyl)-benzamide in Japanese Patent Application No. 59/146050 (21.8.1984; Fuji);

N-[4-(1,1-dimethylethyl)-phenyl]-benzamide in R. M. Acheson, C. W. C. Harvey, J. Chem. Soc., Perkin I, 1976; 465;

N-[4-(1,1-dimethylethyl)-phenyl]-4-methylbenzamide in Japanese Patent Application No. 58/187 391 (1.11.1983; Fuji);

methyl 3-[[4-(1,1-dimethylethyl)-benzoyl]-amino]-4-methyl-benzoate and methyl 4-amino-3-[[4-(1,1-dimethylethyl)-benzoyl]-amino]-benzoate in Belgian Patent Specification No. 903,254 (18.3.1986; C.I.R.D.).

The alkyl, alkenyl and alkynyl moieties of the radicals mentioned in the case of the substituents $R_1$, $R_2$, $R_3$, $R_5$ and $R_6$ contain 1 to 6 and 2 to 6 carbon atoms, respectively, and can be straight-chained or branched. Derivatives with 1 to 4 and 2 to 4 carbon atoms, respectively, are preferred.

There are preferably understood thereunder the methyl, ethyl, n-propyl, isopropyl, n-butyl, isobutyl, tert.-butyl, pentyl, hexyl, methoxy, ethoxy, n-propyloxy, isopropoxy, allyloxy, isobutenyloxy, propynyloxy, n-butyloxy, tert.-butoxy, isobutoxy, n-pentoxy, n-hexyloxy, methylsulphonyloxy, ethylsulphonyloxy, n-propylsulphonyloxy, isopropylsulphonyloxy, methylcarbonyloxy, ethylcarbonyloxy, propylcarbonyloxy, cyanoethyloxy, carboxyethoxy, ethoxycarbonylethoxy, methoxycarbonylethoxy, methoxyethoxy, dimethylamino, diethylamino, acetylamino, propionylamino, methylsulphonylamino, ethylsulphonylamino, n-propylsulphonylamino, isopropylsulphonylamino, acetylaminocarbonylamino, propionylaminocarbonylamino, acetyl, propionyl, ethoxycarbonyl, propoxycarbonyl, butoxycarbonyl, methylaminocarbonyl, ethylaminocarbonyl, propylaminocarbonyl, dimethylaminocarbonyl, diethylaminocarbonyl, methylaminosulphonyl, ethylaminosulphonyl, methylthio, ethylthio, propylthio, methylsulphinyl, ethylsulphinyl, propylsulphinyl, methylsulphonyl, ethylsulphonyl, and propylsulphonyl radicals.

Further substituents $R_1$, $R_2$ and $R_3$ which are preferred include the phenyl radical when $R_1$, $R_2$ or $R_3$ is a substituted hydroxyl group, or a phenyloxy, pyridinyloxy and benzyloxy radical; furthermore, halogen atoms, such as fluorine, chlorine or bromine, nitro, amino, formyl, hydroxyl, mercapto, cyano, formylamino, carboxyl, piperidinosulphonyl, morpholinosulphonyl and the thiomorpholinosulphonyl group, as well as the hydrogen atom.

If ortho-positioned substituents $R_1$ and $R_2$, together with the carbon atoms to which they are attached, form a five- or six-membered ring, then bicyclic radicals result therefrom, amongst which the methylenedioxyphenyl, ethylenedioxyphenyl and tetrahydronaphthyl radicals are to be understood.

Especially preferred for $R_1$ is a hydrogen atom or methyl, ethyl, n-propyl, isopropyl, n-butyl, tert.-butyl, fluoro-, chloro-, bromo-, nitro-, amino, hydroxyl, mercapto, formyl, cyano, formylamino, carboxyl, $C_1$-$C_4$-alkyl, $C_1$-$C_4$-alkoxy, allyloxy, isobutenyloxy, propargyloxy, cyanomethoxy, ethoxycarbonylmethoxy, aminocarbonyl, methoxycarbonyl, ethoxycarbonyl, $C_1$-$C_3$-dialkylamino, $C_1$-$C_3$-alkylthio, $C_1$-$C_3$-alkylsulphinyl, $C_1$-$C_3$-alkylsulphonyl, $C_1$-$C_3$-alkylsulphonyloxy, phenyl, phenyloxy, pyridinyloxy and benzyloxy; for $R_2$ a hydrogen atom or $C_1$-$C_4$-alkyl, $C_1$-$C_4$-alkoxy, $C_1$-$C_3$-dialkylamino, fluoro, chloro, bromo or hydroxyl; and for $R_3$ a hydrogen atom or hydroxyl or methoxy.

Preferred monosubstituted phenyls include the fluoro-, chloro-, bromo-, hydroxy-, amino-, cyano-, $C_1$-$C_4$-alkyl-, $C_1$-$C_4$-alkoxy-, $C_2$-$C_4$-alkenyloxy-, propargyloxy-, cyanomethoxy-, methoxycarbonylmethoxy-, nitro-, aminocarbonyl-, methoxycarbonyl-, ethoxycarbonyl-, $C_1$-$C_3$-dialkylamino-, $C_1$-$C_3$-alkylthio-, $C_1$-$C_3$-alkylsulphinyl-, $C_1$-$C_3$-alkylsulphonyl-, $C_1$-$C_3$-alkylsulphonyloxy-, trifluoromethylsulphonyloxy-phenyls, the substituent being in the 2-, 3- or 4-position.

Preferred disubstituted phenyls contain, as substituents, $C_1$-$C_4$-alkyl, chloro, hydroxyl, $C_1$-$C_4$-alkoxy, methylenedioxy, $C_1$-$C_4$-alkylsulphonyloxy, trifluoromethylsulphonyloxy, $C_1$-$C_4$-alkylthio, $C_1$-$C_4$-alkylsulphinyl, $C_1$-$C_4$-alkylsulphonyl, $C_1$-$C_4$-alkylsulphonylamino, trifluoromethylsulphonylamino, cyanomethoxy or methoxycarbonylmethoxy, in which case the substituents can be the same or different and can be in the 2,3-, 2,4-, 2,5-, 2,6-, 3,4- or 3,5-position.

Preferred trisubstituted phenyls can contain, as substituents, $C_1$-$C_4$-alkyl, $C_1$-$C_4$-alkenyl, $C_1$-$C_4$-alkenyloxy or chloro, in which case the substituents can be the same or different and can be in the 2,3,4-, 2,3,5-, 2,3,6-, 2,4,5-, 2,4,6- or 3,4,5-position.

If, in general formula (I), X is an alkylene radical, then this is to be understood to include the methylene, ethylene, propylene and butylene radicals. As alkenylene radical, the vinylene radical is especially preferred.

If, in general formula (I), $R_5$ or $R_6$ is an alkyl radical, then this is to be understood to be a straight-chained or branched alkyl chain containing up to 6 carbon atoms, the methyl, ethyl, propyl and butyl radicals being preferred.

If, in general formula (I), $R_6$ is a cycloalkyl radical, then this is preferably a cyclopropyl, cyclobutyl, cyclopentyl or cyclohexyl radical.

If, in general formula (I), $R_5$ and $R_6$, together with the carbon atom to which they are attached, form a cycloalkyl ring, then the cyclopropyl, cyclobutyl, cyclopentyl and cyclohexyl rings are preferred.

If $R_1$ is in the ortho-position of the phenyl ring, then, within the scope of the present invention, $R_1$ is preferably a hydrogen or chlorine atom, a $C_1$-$C_4$-alkoxy radical, for example a methoxy radical, or a nitro group.

If $R_2$ is a substituent in the meta-position, then this is preferably a hydrogen or chlorine atom or a $C_1$-$C_4$-alkoxy radical, for example a methoxy radical.

When $R_3$ is in the para-position of the phenyl ring, then this is preferably one of the following: a hydrogen or halogen atom, a $C_1$-$C_4$-alkyl radical, for example a methyl radical, a $C_2$-$C_4$-alkenyl radical, for example an allyl radical, a nitro, amino, hydroxyl or cyano group, a $C_1$-$C_4$-alkoxy radical, for example a methoxy or n-propoxy radical, benzyloxy, pyridinyloxy, $C_1$-$C_4$-alkylsulphonyloxy radical, for example a methylsulphonyloxy radical, a hydroxy-$C_1$-$C_4$-alkoxy radical, for example a hydroxyethoxy radical, a carboxy-$C_1$-$C_4$-alkoxy radical, for example a carboxymethoxy or carboxypropoxy radical, a $C_1$-$C_4$-alkoxycarbonyl-$C_1$-$C_4$-alkoxy, for example an ethoxycarbonylmethoxy or ethoxycarbonylpropoxy radical, a di-$C_1$-$C_4$-alkylamino radical, for example a dimethylamino radical, or an N-$C_5$-$C_6$-cycloalkyl-N-$C_1$-$C_4$-alkylaminocarbonyl- $C_1$-$C_4$-alkoxy radical, for example an N-cyclohexyl-N-methylaminocarbonylpropoxy radical.

$R_4$ is especially preferably a methyl radical or a cyano group. In the definition of $R_5$, a $C_1$-$C_4$-alkyl radical, for example a methyl radical, or a hydrogen atom is preferred.

For $R_6$ there is especially preferred an alkyl radical, for example a methyl radical. However, $R_5$ and $R_6$, together with the carbon atom to which they are attached, can also represent a cyclopentyl or cyclohexyl ring.

X is preferably a valency bond.

Especially preferred pharmaceutical compositions according to the present invention contain compounds of the general formula (I) in which $R_1$ can be hydrogen, nitro, amino, fluoro, chloro, bromo, dimethylamino, diethylamino, cyano, methyl, ethyl, n-propyl, isopropyl, n-butyl, isobutyl, tert.-butyl, allyl, hydroxyl, methoxy, ethoxy, propoxy, allyloxy, mercapto, methylthio, methylsulphinyl, methylsulphonyl, methylsulphonyloxy, cyanomethoxy, benzyloxy, pyridinyloxy, ethoxycarbonylmethoxy, carboxyl, ethoxycarbonyl, hydroxymethyl, formylamino, acetylamino, methylsulphonylamino or trifluoromethylsulphonylamino; $R_2$ is hydrogen, methyl, ethyl, n-propyl, isopropyl, tert.-butyl, chloro, methoxy, hydroxyl or dimethylamino; $R_3$ is hydrogen, hydroxyl or methoxy; X is a valency bond or an ethylene radical or, when A is a carbonyl group, also a vinylene radical, A and B are different and are imino or carbonyl groups, $R_4$ is methyl, cyano, aminocarbonyl or aminomethyl, $R_5$ is hydrogen, methyl or ethyl, $R_6$ is methyl, ethyl or cyclopentyl or $R_5$ and $R_6$, together with the carbon atom to which they are attached, is a cyclopentyl radical.

The present invention also provides new compounds of the general formula:

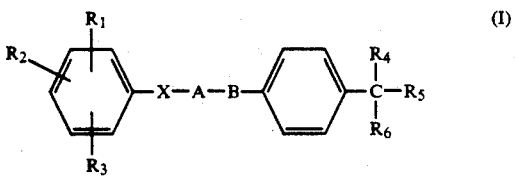

(I)

wherein $R_1$, $R_2$ and $R_3$ can be the same or different and each represents hydrogen, alkyl, alkenyl, alkynyl, cycloalkyl, cycloalkenyl, phenyl, halogen, nitro, amino, formyl, hydroxyl, mercapto or cyano, or a hydroxyl group substituted by alkyl, alkenyl, alkynyl, cycloalkyl, cycloalkenyl, benzyl, pyridinyl, alkylsulphonyl, trifluoromethylsulphonyl, alkylcarbonyl, cyanoalkyl, hydroxyalkyl, dialkylaminoalkyl, carboxyalkyl, alkoxycarbonylalkyl or alkoxyalkyl, or an amino group substituted once or twice by alkylsulphonyl, trifluoromethylsulphonyl, alkylcarbonyl, formyl, aminocarbonyl, alkylaminocarbonyl or alkyl or a carbonyl group substituted by hydroxyl, alkyl, alkoxy, amino, alkylamino or dialkylamino, or a sulphonyl group substituted by amino, alkylamino, piperidino, morpholino or thiomorpholino; or alkylthio, alkylsulphinyl or alkylsulphonyl or in the case of two substituents $R_2$ and $R_3$ standing ortho to one another, together with the carbon atoms to which they are attached, form a five- or six-membered ring, X is a valency bond or an alkylene radical or, when A is a carbonyl group —CO—, can also be a vinylene radical, A and B are different and are the carbonyl group —CO— or the imino group —NH—, $R_4$ is methyl, cyano, aminocarbonyl or aminomethyl, $R_5$ is a hydrogen atom or an alkyl radical and $R_6$ is an alkyl or cycloalkyl radical or $R_5$ and $R_6$, together with the carbon atom to which they are attached, form a cycloalkyl radical, the tautomers thereof, the physiologically acceptable salts thereof, as well as the optical isomers thereof, with the exception of the following compounds:

4-(1,1-dimethylethyl)-N-[3-trifluoromethyl)-phenyl]-benzamide, N-[4-chloro-3-trifluoromethyl)-phenyl]-4-(1,1-dimethylethyl)-benzamide, 4-(1,1-dimethylethyl)-N-[2-(1H-imidazol-1-yl)-phenyl]-benzamide, N-[2-(aminocarbonyl)-phenyl]-4-(1,1-dimethylethyl)-benzamide, 4-(1,1-dimethylethyl)-N-phenylbenzamide, N-(2,6-dihydroxyphenyl)-4-(1,1-dimethylethyl)-benzamide, 4-(1,1-dimethylethyl)-N-[2-(1-methylethoxy)-phenyl]-benzamide, methyl 2-[[4-(1,1-dimethylethyl)-benzoyl]-amino]-benzoate, N-(2,3-dichlorophenyl)-4-(1,1-dimethylethyl)-benzamide, 4-(1,1-dimethylethyl)-N-[4-(1-methylethoxy)-phenyl]-benzamide, 4-(1,1-dimethylethyl)-N-[4-(1,1-dimethylethyl)-phenyl]-benzamide, 4-(1,1-dimethylethyl)-N-(3-ethyl-4-hydroxyphenyl)-benzamide, 4-(1,1-dimethylethyl)-N-[3-(1,1-dimethylethyl)-4-hydroxy-5-methylphenyl]-benzamide, 4-(1,1-dimethylethyl)-N-(2-hydroxy-4-nitrophenyl)-benzamide, N-(5-chloro-2-hydroxy-4-nitrophenyl)-4-(1,1-dimethylethyl)-benzamide, N-(4-amino-5-chloro-2-hydroxyphenyl)-4-(1,1-dimethylethyl)-benzamide, N-[4-(1,1-dimethylethyl)-phenyl]-benzamide, N-[4-(1,1-dimethylethyl)-phenyl]-4-benzamide, methyl 3-[[4-(1,1-dimethylethyl)-benzoyl]-amino]-4-methylbenzoate and methyl 4-amino-3-[[4-(1,1-dimethylethyl)-benzoyl]-amino]-benzoate.

The compounds of general formula (I) according to the present invention can be prepared by known methods. Of especial advantage is the synthesis from anilines and benzoic acids as is described in the following schemes 1 and 2. For compounds of general formula (I) in which A is an imino group —NH— and B is a carbonyl group —CO— (=general formula Ia), anilines of the general formula (II), in which $R_1$, $R_2$, $R_3$ and X have the above-given meanings, are reacted with benzoic acids of the general formula (III), in which $R_4$, $R_5$ and $R_6$ have the above-given meanings and Y is a hydroxyl group, a halogen atom, for example chlorine or bromide, or an alkoxy, aryloxy, alkylcarbonyloxy or arylcarbonyloxy radical (scheme 1):

Scheme 1:

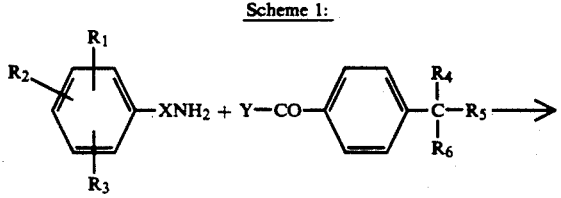

(II)                    (III)

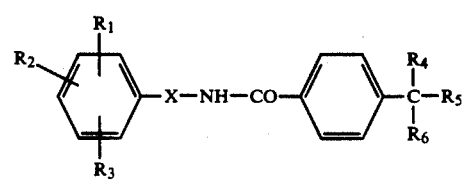

(Ia)

For compounds of general formula (I) in which A is a carbonyl group —CO— and B an imino group —NH— (=general formula Ib), benzoic acids of general formula (IV), in which $R_1$, $R_2$, $R_3$ and X have the above-given meanings, are reacted with anilines of the general formula (V), in which $R_4$, $R_5$ and $R_6$ have the above-given meanings (scheme 2):

Scheme 2:

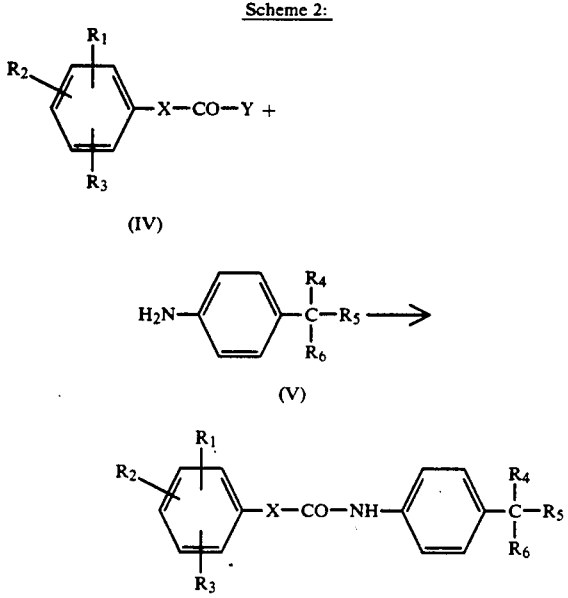

A survey of the methods used for the preparation of compounds of general formula (I) is given by D. Döpp and H. Döpp in J. Falbe (editor), Methoden der Organischen Chemie (Houben-Weyl), publ. Verlag Thieme, Stuttgart, New York, 1985, pp. 934 et seq.

If, in general formula (III) or (IV), Y is a hydroxyl group, then the compounds of general formula (III) or (IV) are carboxylic acids. A preferred method for the reaction with the amines of general formula (II) or (V) consist in the reaction of about equimolar amounts of the amines and of the acid in the presence of an agent removing water. For this purpose, there can be used, for example, polyphosphoric acid which then simultaneously serves as solvent. The reaction takes place at a temperature of from 50° to 200° C. The end products of general formula (I) generally precipitate out upon the addition of water and, after filtration, are purified by recrystallisation or column chromatography. A further preferred method for the preparation of compounds of general formula (I) consists in the reaction of about equimolar amounts of the amine and of the acid in an appropriate solvent with about one equivalent amount of a halogenation agent, for example phosphorus trichloride, phosphorus pentachloride or thionyl chloride, at a temperature of from ambient temperature to the reflux temperature of the reaction mixture. Appropriate solvents include methylene chloride, carbon tetrachloride, diethyl ether, toluene, xylene and chlorobenzene. In general, the product precipitates out of the solution and is obtained by filtration. If necessary, the reaction mixture can be concentrated up to a point at which the product begins to precipitate out of the solution. As further condensation agents in the case of this reaction, there can be used acidic cation exchangers, sulphonium salts, sulphuric acid halides, 2-halopyridinium salts, phosphonium salts and dicyclohexylcarbodiimide.

If, in general formula (III) or (IV), Y is an alkoxy or aryloxy radical, then the compounds of general formula (III) or (IV) are carboxylic acid esters. The reaction can be carried out in the presence or absence of special solvents at a temperature of from 20° C. to the boiling temperature of the reaction mixture. The reaction of about equimolar amounts of the amine and of the ester in polyphosphoric acid at a temperature of from 50° to 200° C. is thereby preferred but it is also preferred to work in an inert solvent, for example methylene chloride, benzene, toluene or chlorobenzene, best in the presence of somewhat more than one equivalent of a base, for example sodium ethanolate or butyl lithium, or of sodium hydride in dimethyl sulphoxide.

If, in general formula (III) or (IV), Y is an alkylcarbonyloxy or arylcarbonyloxy radical, then the compounds of general formula (III) or (IV) are anhydrides. Since, in general, anhydrides are more reactive than carboxylic acids or carboxylic acid esters, the reaction with the amines of the general formula (II) or (V) can already be carried out at somewhat lower temperatures. It is preferred to work in an inert solvent, for example dichloromethane, diethyl ether, benzene or toluene, at a temperature of from ambient temperature to 60° C. The amine and the anhydride are mixed together in approximately equimolar amounts, an exothermal reaction thereby generally taking place. After subsidence of the reaction, the reaction mixture is gently warmed for some time for completion of the reaction.

If, in general formula (III) or (IV), Y is a halide, then the compounds of general formula (III) or (IV) are carboxylic acid halides. These are to be understood to include, in particular, acid chlorides and bromides. Since the acid halides are more reactive than the carboxylic acids, esters and anhydrides, it is usually necessary to cool the reaction mixture. It is preferred to work at a temperature of from −10° C. to ambient temperature.

It is preferred to proceed in such a manner that, according to Schotten-Baumann, to an aqueous solution of the amine of general formula (II) or (V), which also contains a base, for example an alkali metal hydroxide, sodium carbonate or pyridine, there is slowly added dropwise the acid chloride, with ice cooling, whereafter the reaction mixture is left to stand for some time at ambient temperature. This reaction is possible not only in water but also in an organic solvent, for example methylene chloride, diethyl ether, benzene or toluene. The amines can also be acylated almost quantitatively by carboxylic acid chlorides without the use of an acid-binding agent by boiling the amine and the carboxylic acid chloride in an inert solvent, for example methylene chloride, benzene or toluene, up to the end of the gas evolution, which lasts about 1 to 24 hours. If, however, an acid-binding agent, for example triethylamine or pyridine, is added thereto in slight excess, then the reaction already takes place at a temperature of from −10° C. to ambient temperature.

Compounds of general formula (I) can also be converted into other compounds of general formula (I) This applies to the following cases:

a) For the alkylation of compounds of general formula (I) in which one or more of the substituents $R_1$ $R_2$ and $R_3$ is a hydroxyl or mercapto group, to give the corresponding alkoxy or alkylthio compounds. These reactions are preferably carried out in a solvent, for example acetone, diethyl ether, benzene, toluene or dimethylformamide, at a temperature of from −30° to +100° C. and preferably at ambient temperature in the presence of a base, for example potassium hydroxide, and of an alkylation agent, for example an alkyl halide or alkyl sulphate.

b) For the preparation of compounds of general formula (I), in which $R_1$ is an alkylsulphinyl or alkylsulphonyl radical, by subsequent oxidation of a compound in which $R_1$ is an alkylthio radical. The oxidation is preferably carried out in a solvent or solvent mixture, for example water, water/pyridine, acetone, glacial acetic acid, dilute sulphuric acid or trifluoroacetic acid, depending upon the oxidation agent used, advantageously at a temperature of from −80° to +100° C.

For the preparation of an alkylsulphinyl compound of general formula (I), the oxidation is advantageously carried out with one equivalent of the oxidation agent used, for example with hydrogen peroxide, in glacial acetic acid, trifluoroacetic acid or formic acid at 0° to 20° C. or in acetone at 0° to 60° C., with a per acid, for example performic acid in glacial acetic acid or trifluoroacetic acid at 0° to 50° C. or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, with N-bromosuccinimide in ethanol, with tert.-butyl hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphuryl chloride in methylene chloride at −70° C., the thioether chlorine complex thereby obtained advantageously being hydrolysed with aqueous ethanol.

For the preparation of an alkylsulphonyl compound of general formula (I), the oxidation is advantageously carried out with one or with two more equivalents of the oxidation agent used, for example hydrogen peroxide in glacial acetic acid, trifluoroacetic acid or in formic acid at 20° to 100° C. or in acetone at 0° to 60° C., with a per acid, for example performic acid or m-chloroperbenzoic acid in glacial acetic acid, trifluoroacetic acid, methylene chloride or chloroform at a temperature of from 0° to 60° C., with nitric acid in glacial acetic acid at 0° to 20° C., with chromic acid or potassium permanganate in glacial acetic acid, water/sulphuric acid or in acetone at 0° to 20° C.

c) For the preparation of compounds of the general formula (I), in which $R_1$ is an alkanesulphonyloxy, trifluoromethanesulphonyloxy, alkanesulphonylamino or trifluoromethanesulphonylamino radical, by the subsequent reaction of a compound in which $R_1$ is a hydroxyl group with a sulphonic acid of the general formula:

$$R_7-SO_3H \qquad (VI)$$

in which $R_7$ is an alkyl or trifluoromethyl radical, in the presence of an agent removing water and/or activating the acid or the amine or with a reactive derivative thereof.

The reaction is advantageously carried out in a solvent or solvent mixture, for example methylene chloride, diethyl ether, tetrahydrofuran, dioxan or benzene, optionally in the presence of an acid-binding agent, for example sodium carbonate, triethylamine or pyridine, in which case the latter two can also be used as solvent, in the presence of an agent activating the acid or removing water, for example thionyl chloride or phosphorus pentachloride, but preferably with a reactive derivative of a compound of general formula (VII), for example an anhydride or a halide thereof, for example methanesulphonic acid chloride or ethanesulphonic acid chloride, preferably at a temperature of from 0° to 100° C., for example at a temperature of from ambient temperature to 50° C.

d) For the preparation of compounds of general formula (I), in which $R_1$ is a formyl radical substituted by amino, alkylamino or dialkylamino, by the subsequent reaction of a compound in which $R_1$ is a carboxyl group or a reactive derivative thereof, for example an ester or acid chloride, with an amine of the general formula:

$$R_8-NH-R_9 \qquad (VII)$$

in which $R_8$ and $R_9$, which can be the same or different, are hydrogen atoms or alkyl radicals or with a reactive derivative thereof if $R_1$ is a carboxyl group. The reaction is advantageously carried out in a solvent, for example methylene chloride, ethanol, chloroform, carbon tetrachloride, diethyl ether, tetrahydrofuran, dioxan, benzene, toluene, acetonitrile or dimethylformamide, optionally in the presence of an agent activating the acid or of an agent removing water, for example in the presence of ethyl chloroformate, thionyl chloride, phosphorus trichloride, phosphorus pentoxide, N,N'-dicyclohexylcarbodiimide/N-hydroxysuccinimide, N,N'-carbonyldiimidazole or N,N'-thionyldiimidazole or triphenyl phosphine/carbon tetrachloride, or of an agent activating the amino group, for example phosphorus trichloride, and possibly in the presence of an inorganic base, for example sodium carbonate, or of a tertiary organic base, for example triethylamine or pyridine, which can simultaneously serve as solvent, at a temperature of from −25° to 250° C. but preferably at a temperature of from −10° C. to the boiling temperature of the solvent used. Furthermore, water formed during the reaction can be separated off by azeotropic distillation, for example by heating with toluene on a water separator, or by the addition of a drying agent, for example anhydrous magnesium sulphate or a molecular sieve.

However, the reaction is carried out especially advantageously with a corresponding halide, for example the carboxylic acid chloride and a corresponding amine, in which case this can simultaneously serve as solvent, and at a temperature of from 0° to 50° C.

e) The saponification of compounds of general formula (I), in which $R_1$ or $R_4$ is a cyano group, to give compounds of general formula (I), in which $R_1$ or $R_4$ is an aminocarbonyl group. Working is carried out in the presence of an acid, for example hydrochloric acid, sulphuric acid, phosphoric acid or trichloroacetic acid, or in the presence of a base, for example sodium hydroxide or potassium hydroxide, in an appropriate solvent, for example water, methanol, water/methanol, water/ethanol, ethanol, water/isopropanol or water/dioxan, at a temperature of from ambient temperature to the boiling temperature of the reaction mixture or in an inert solvent, for example dichloromethane, with the addition of a phase transfer catalyst, for example tetrabutylammonium hydrogen sulphate, with the addition of hydrogen peroxide, in which case it is possible to work at ambient temperature.

f) The reduction of compounds of general formula (I), in which one of the substituents $R_1$, $R_2$ or $R_3$ is a nitro group, to give compounds of the general formula (I), in which $R_1$, $R_2$ or $R_3$ is an amino group. The hydrogenation is preferably carried out in a solvent, for example water, ethanol, glacial acetic acid, ethyl acetate or dimethylformamide, with hydrogen in the presence of a catalyst, for example Raney nickel, platinum or palladium/charcoal, with metals, such as iron, tin or zinc, in the presence of an acid, with salts, for example ferrous sulphate, stannous chloride, sodium sulphide, sodium hydrogen sulphide or sodium dithionite, or with hydrazine in the presence of Raney nickel at a temperature of from 0° to 250° C. but preferably at ambient temperature.

g) The hydrogenation of a compound of general formula (I), in which X is a vinylene radical, to give a compound of general formula (I), in which X is an ethylene radical.

The hydrogenation is preferably carried out in a solvent, for example water, water/ethanol, methanol, glacial acetic acid, ethyl acetate or dimethylformamide, in the presence of hydrogen and a catalyst, for example Raney nickel, platinum or palladium/charcoal.

h) The reduction of compounds of general formula (I), in which $R_4$ is a cyano group, to give compounds of general formula (I), in which $R_4$ is an aminomethyl radical. This reduction is carried out with hydrogen under pressure in the presence of ammonia and of a catalyst, for example Raney nickel, preferably at a temperature of from 50° to 150° C. and at a pressure of from 50 to 250 bar.

i) The reduction of a compound of general formula (I), in which one of the substituents $R_1$, $R_2$ or $R_3$ contains an alkoxycarbonyl radical, to give the corresponding hydroxyalkyl compound. This reduction is preferably carried out with lithium aluminium hydride in an ether, for example diethyl ether or dioxan, at the boiling point of the solvent.

j) The saponification of a compound of general formula (I), in which one of the substituents $R_1$, $R_2$ or $R_3$ contains an alkoxycarbonyl radical, to give the corresponding hydroxycarbonyl compound. Such saponifications are preferably carried out in aqueous or aqueous alcoholic sodium hydroxide solution or potassium hydroxide solution, the acid then being liberated by acidification with a mineral acid.

k) The nitration of compounds of general formula (I), in which X is a valency bond, A is an imino group —NH— and B is a carbonyl group —CO—. Compounds are thereby formed in which one of the substituents $R_1$, $R_2$ or $R_3$ is a nitro group which enters into the ortho-position for the amide function A-B (=—NH—CO—).

The nitration is preferably carried out with nitric acid in sulphuric acid at a temperature of from −20° C. to +50° C. However, it can also be carried out without sulphuric acid or, in place thereof, in water, glacial acetic acid or acetic anhydride, or with $N_2O_5$ in carbon tetrachloride in the presence of phosphorus pentoxide. As nitrating agents, there can also be used anhydrides, for example acetyl nitrate, or nitryl halides with ferric chloride, methyl nitrate and boron trifluoride, or nitronium salts, for example $NO_2BF_4$, $NO_2PF_6$ or $NO_2CF_3SO_3$. For the nitration, there can also be used a mixture of nitric acid and nitrous acid which provides $N_2O_4$ as the actual nitrating species.

The anilines of general formula (II) required as precursors for the preparation of compounds of general formula (I) according to scheme 1 and 2 and the benzoic acids of general formula (IV) are commercially available or known from the literature. Of the anilines of general formula (V), 4-tert.-butylaniline is commercially available and the others are known from the literature (cf. Jönsson, Acta chem. Scan., 8, 1211/1954; Nerdel, Würgau, Liebigs Ann. Chem., 621, 34/1959) or can be prepared by the methods described therein.

Scheme III

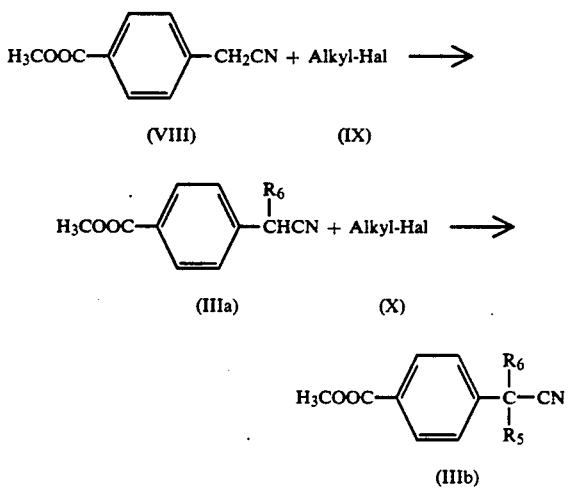

Compounds of the general formula (III), in which $R_4$ is a cyano group, $R_5$ and $R_6$ have the above-given meanings and Y is an alkoxy radical (=general formula (IIIa) and (IIIb)) are prepared by the stepwise alkylation of 4-(cyanomethyl)-benzoic acid esters, for example of the compound (VIII), with the alkylation agents of general formulae (IX) and (X) in which alkyl is a $C_1$-$C_6$-alkyl radical or a $C_3$-$C_6$-cycloalkyl radical and Hal is a halogen atom, preferably a chlorine or bromine atom. The compounds of general formulae (IX) or (X) can be the same or different. If, in general formula (III), $R_5$ and $R_6$, together with the carbon atom to which they are attached, form a cycloalkyl ring and $R_4$ is a cyano group and Y an alkoxy radical (=general formula (IIIc)), then the alkylation of the compound (VIII) is carried out with an alkylene dihalide of general formula (XI):

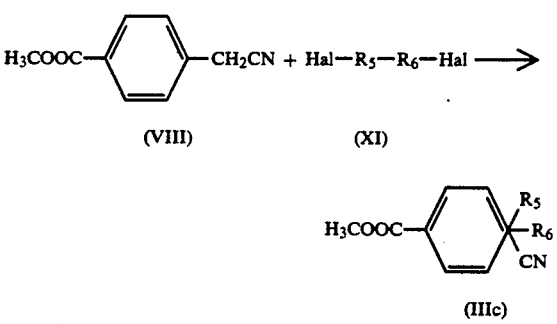

This alkylation is carried out in an inert solvent, for example dichloromethane, diethyl ether, toluene or xylene, in the presence of a base, for example an aqueous solution of sodium or potassium hydroxide, if desired in the presence of a phase transfer catalyst, for example tetrabutylammonium bromide, and an equivalent of the alkylation agent (IX), (X) or (XI).

The compound (VIII) is known from the literature (J. F. Codington, E. Mosettig, J. Org.Chem., 17, 1035/1952).

A further process for the preparation of compounds of general formula (III) starts from anilines of general formula (V):

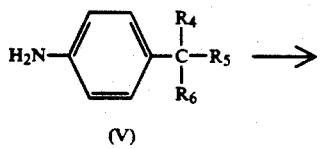

(V)

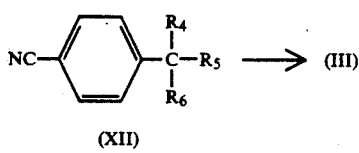

(XII)

By the reaction sequence diazotisation, cyanation (Sandmeyer reaction) and saponification of the nitrile, there can be obtained the compounds of general formula (III).

The compounds of general formula (I) can also be used as starting materials for the preparation of other pharmaceutically-useful compounds which are the subject of Federal Republic of Germany Patent Application No. P 38 30 060.5.

For the preparation of pharmaceutical compositions, the compounds of general formula (I) are mixed in known manner with appropriate pharmaceutical carrier materials, aroma, flavouring and colouring materials and formed, for example, into tablets or dragrees or, with the addition of appropriate adjuvants, suspended or dissolved in water or an oil, for example olive oil.

The compounds of general formula (I) and the salts thereof can be administered enterally or parenterally in liquid or solid form. As injection medium, it is preferred to use water which contains the additives usual in the case of injection solutions, such as stabilizing agents, solubilising agents and/or buffers.

Additives of this type include, for example tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

If desired, compounds of general formula (I) can be converted into their physiologically acceptable salts with inorganic and organic acids. As acids, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

The compounds are usually administered in amounts of from 10 to 1500 mg. per day, referred to a body weight of 75 kg. It is preferred to administer 2 to 3 times a day 1 or 2 tablets with a content of active material of 5 to 500 mg. The tablets can also be retarded, in which case only 1 or 2 tablets containing 20 to 700 mg. of active material have to be given once per day. The active material can also be administered by injection 1 to 8 times a day or by continuous infusion, in which case amounts of 10 to 1000 mg. per day normally suffice.

Preferred according to the present invention are, apart from the compounds mentioned in the Examples, also the following compounds:

N-(2-hydroxyphenyl)-4-(1,1-dimethylethyl)-benzamide
N-(2-(methoxycarbonyl)-phenyl)-4-(1,1-dimethylethyl)-benzamide
N-(2-ethylphenyl)-4-(1,1-dimethylethyl)-benzamide
N-(2-mercaptophenyl)-4-(1,1-dimethylethyl)-benzamide
N-(2-cyanophenyl)-4-(1,1-dimethylethyl)-benzamide
N-(2-(ethoxy)-phenyl)-4-(1,1-dimethylethyl)-benzamide
N-(2-methylphenyl)-4-(1,1-dimethylethyl)-benzamide
N-(2-(sec.-butyl)-phenyl)-4-(1,1-dimethylethyl)-benzamide
N-(2-(hydroxymethyl)-phenyl)-4-(1,1-dimethylethyl)-benzamide
N-(2-carboxyphenyl)-4-(1,1-dimethylethyl)-benzamide
N-(2-ethoxycarbonyl)-phenyl)-4-(1,1-dimethylethyl)-benzamide
N-(2-biphenyl)-4-(1,1-dimethylethyl)-benzamide
N-(2-fluorophenyl)-4-(1,1-dimethylethyl)-benzamide
N-(2-nitrophenyl)-4-(1,1-dimethylethyl)-benzamide
N-(2-aminophenyl)-4-(1,1-dimethylethyl)-benzamide
N-(2-bromophenyl)-4-(1,1-dimethylethyl)-benzamide
N-(2-iodophenyl)-4-(1,1-dimethylethyl)-benzamide
N-(2-acetylphenyl)-4-(1,1-dimethylethyl)-benzamide
N-(2-allyloxyphenyl)-4-(1,1-dimethylethyl)-benzamide
N-(3-carboxylphenyl)-4-(1,1-dimethylethyl)-benzamide
N-(3-hydroxyphenyl)-4-(1,1-dimethylethyl)-benzamide
N-(3-nitrophenyl)-4-(1,1-dimethylethyl)-benzamide
N-(3-aminophenyl)-4-(1,1-dimethylethyl)-benzamide
N-(3-methylphenyl)-4-(1,1-dimethylethyl)-benzamide
N-(3-ethylphenyl)-4-(1,1-dimethylethyl)-benzamide
N-(3-cyanophenyl)-4-(1,1-dimethylethyl)-benzamide
N-(3-hydroxymethylphenyl)-4-(1,1-dimethylethyl)-benzamide
N-(3-acetylphenyl)-4-(1,1-dimethylethyl)-benzamide
N-(3-dimethylaminophenyl)-4-(1,1-dimethylethyl)-benzamide
N-(3-fluorophenyl)-4-(1,1-dimethylethyl)-benzamide
N-(3-iodophenyl)-4-(1,1-dimethylethyl)-benzamide
N-(3-ethyloxyphenyl)-4-(1,1-dimethylethyl)-benzamide
N-(3-bromophenyl)-4-(1,1-dimethylethyl)-benzamide
N-(3-allyloxyphenyl)-4-(1,1-dimethylethyl)-benzamide
N-(4-acetylaminophenyl)-4-(1,1-dimethylethyl)-benzamido
N-(4-acetylphenyl)-4-(1,1-dimethylethyl)-benzamide
N-(4-hydroxyphenyl)-4-(1,1-dimethylethyl)-benzamide
N-(4-carboxymethylphenyl)-4-(1,1-dimethylethyl)-benzamide
N-(4-ethylphenyl)-4-(1,1-dimethylethyl)-benzamide
N-(4-aminocarbonylphenyl)-4-(1,1-dimethylethyl)-benzamide
N-(4-bromophenyl)-4-(1,1-dimethylethyl)-benzamide
N-(4-ethyloxyphenyl)-4-(1,1-dimethylethyl)-benzamide
N-(4-sec.-butylphenyl)-4-(1,1-dimethylethyl)-benzamide
N-(4-butylphenyl)-4-(1,1-dimethylethyl)-benzamide
N-(4-isopropylphenyl)-4-(1,1-dimethylethyl)-benzamide
N-4-[N'-ethyl-N'-(2-hydroxyethyl)-aminophenyl]-4-(1,1-dimethylethyl)-benzamide N-(4-propynylphenyl)-4-(1,1-dimethylethyl)-benzamide
N-(4-diethylaminophenyl)-4-(1,1-dimethylethyl)-benzamide
N-(4-fluorophenyl)-4-(1,1-dimethylethyl)-benzamide
N-(4-iodophenyl)-4-(1,1-dimethylethyl)-benzamide
N-(4-methylphenyl)-4-(1,1-dimethylethyl)-benzamide
N-(4-sulphonylphenyl)-4-(1,1-dimethylethyl)-benzamide
N-(4-carboxyphenyl)-4-(1,1-dimethylethyl)-benzamide
N-(4-allyloxyphenyl)-4-(1,1-dimethylethyl)-benzamide
N-(3-chloro-2-methylphenyl)-4-(1,1-dimethylethyl)-benzamide
N-(2-methyl-3-nitrophenyl)-4-(1,1-dimethylethyl)-benzamide
N-(2-methyl-3-aminophenyl)-4-(1,1-dimethylethyl)-benzamide
N-(5,6,7,8-tetrahydronaphthalin-1-yl)-4-(1,1-dimethylethyl)-benzamide
N-(2,3-dichlorophenyl)-4-(1,1-dimethylethyl)-benzamide
N-(2,3-dimethylphenyl)-4-(1,1-dimethylethyl)-benzamide
N-(4-hydroxy-2-methylphenyl)-4-(1,1-dimethylethyl)-benzamide
N-(2,4-dimethoxyphenyl)-4-(1,1-dimethylethyl)-benzamide
N-(2-chloro-4-nitrophenyl)-4-(1,1-dimethylethyl)-benzamide
N-(4-chloro-2-nitrophenyl)-4-(1,1-dimethylethyl)-benzamide
N-(4-chloro-2-aminophenyl)-4-(1,1-dimethylethyl)-benzamide
N-(4-chloro-2-methylphenyl)-4-(1,1-dimethylethyl)-benzamide
N-(2,4-dinitrophenyl)-4-(1,1-dimethylethyl)-benzamide
N-(2,4-diaminophenyl)-4-(1,1-dimethylethyl)-benzamide
N-(2-nitro-4-methoxyphenyl)-4-(1,1-dimethylethyl)-benzamide
N-(2-amino-4-methoxyphenyl)-4-(1,1-dimethylethyl)-benzamide
N-(4-nitro-2-methoxyphenyl)-4-(1,1-dimethylethyl)-benzamide
N-(4-amino-2-methoxyphenyl)-4-(1,1-dimethylethyl)-benzamide
N-(4-nitro-2-methylphenyl)-4-(1,1-dimethylethyl)-benzamide
N-(4-amino-2-methylphenyl)-4-(1,1-dimethylethyl)-benzamide
N-(2-hydroxy-4-methylphenyl)-4-(1,1-dimethylethyl)-benzamide
N-(2-bromo-4-nitrophenyl)-4-(1,1-dimethylethyl)-benzamide
N-(2-bromo-4-aminophenyl)-4-(1,1-dimethylethyl)-benzamide
N-(2,4-dichlorophenyl)-4-(1,1-dimethylethyl)-benzamide
N-(2,4-dimethylphenyl)-4-(1,1-dimethylethyl)-benzamide
N-(2,4-difluorophenyl)-4-(1,1-dimethylethyl)-benzamide
N-(4-methyl-2-chlorophenyl)-4-(1,1-dimethylethyl)-benzamide
N-(2,5-dimethoxyphenyl)-4-(1,1-dimethylethyl)-benzamide
N-(2-hydroxy-5-chlorophenyl)-4-(1,1-dimethylethyl)-benzamide
N-(2-methyl-5-chlorophenyl)-4-(1,1-dimethylethyl)-benzamide
N-(2-methoxy-5-nitrophenyl)-4-(1,1-dimethylethyl)-benzamide
N-(2-methoxy-5-aminophenyl)-4-(1,1-dimethylethyl)-benzamide
N-(2-methyl-5-nitrophenyl)-4-(1,1-dimethylethyl)-benzamide
N-(2-methyl-5-aminophenyl)-4-(1,1-dimethylethyl)-benzamide
N-(2,5-dimethylphenyl)-4-(1,1-dimethylethyl)-benzamide
N-(2-nitro-5-chlorophenyl)-4-(1,1-dimethylethyl)-benzamide
N-(2-amino-5-chlorophenyl)-4-(1,1-dimethylethyl)-benzamide
N-(2-methyl-5-fluorophenyl)-4-(1,1-dimethylethyl)-benzamide
N-(2,5-bis-(methoxycarbonyl)-phenyl)-4-(1,1-dimethylethyl)-benzamide
N-(2,5-dichlorophenyl)-4-(1,1-dimethylethyl)-benzamide
N-(2-hydroxy-5-methylphenyl)-4-(1,1-dimethylethyl)-benzamide
N-(2,6-dimethylphenyl)-4-(1,1-dimethylethyl)-benzamide
N-(2,6-dichlorophenyl)-4-(1,1-dimethylethyl)-benzamide
N-(2-methyl-6-nitrophenyl)-4-(1,1-dimethylethyl)-benzamide
N-(2-methyl-6-aminophenyl)-4-(1,1-dimethylethyl)-benzamide
N-(3-chloro-4-methylphenyl)-4-(1,1-dimethylethyl)-benzamide
N-(3-methoxy-4-methylphenyl)-4-(1,1-dimethylethyl)-benzamide
N-(3,4-dimethylphenyl)-4-(1,1-dimethylethyl)-benzamide
N-(3-nitro-4-fluorophenyl)-4-(1,1-dimethylethyl)-benzamide
N-(3-amino-4-fluorophenyl)-4-(1,1-dimethylethyl)-benzamide
N-(1,4-benzodioxan-6-yl)-4-(1,1-dimethylethyl)-benzamide
N-(3-chloro-4-fluorophenyl)-4-(1,1-dimethylethyl)-benzamide
N-(3,4-dichlorophenyl)-4-(1,1-dimethylethyl)-benzamide
N-(3,5-dimethylphenyl)-4-(1,1-dimethylethyl)-benzamide
N-(3,5-dimethoxyphenyl)-4-(1,1-dimethylethyl)-benzamide
N-(2,4,5-trichlorophenyl)-4-(1,1-dimethylethyl)-benzamide
N-(2,4,6-trimethylphenyl)-4-(1,1-dimethylethyl)-benzamide
N-(2,6-dichloro-4-nitrophenyl)-4-(1,1-dimethylethyl)-benzamide
N-(2,6-dichloro-4-aminophenyl)-4-(1,1-dimethylethyl)-benzamide
N-(2,4,6-trichlorophenyl)-4-(1,1-dimethylethyl)-benzamide
N-(2,4,6-tribromophenyl)-4-(1,1-dimethylethyl)-benzamide
N-(3,5-dimethyl-4-hydroxyphenyl)-4-(1,1-dimethylethyl)-benzamide
N-(4-allyloxy-2-methylphenyl)-4-(1,1-dimethylethyl)-benzamide N-(2-allyloxy-4-methylphenyl)-4-(1,1-dimethylethyl)-benzamide
N-(2-allyloxy-5-chlorophenyl)-4-(1,1-dimethylethyl)-benzamide
N-(2-allyloxy-5-methylphenyl)-4-(1,1-dimethylethyl)-benzamide
N-(4-allyloxy-3,5-dimethylphenyl)-4-(1,1-dimethylethyl)-benzamide
N-(4-(1,1-dimethylethyl)-phenyl)-(4-methoxyphenyl)-benzamide
N-(4-(1,1-dimethylethyl)-phenyl)-4-hydroxybenzamide
N-(4-(1,1-dimethylethyl)-phenyl)-4-propoxybenzamide
N-(4-(1,1-dimethylethyl)-phenyl)-4-allyloxybenzamide
N-(4-(1,1-dimethylethyl)-phenyl)-4-benzyloxybenzamide
N-(4-(1,1-dimethylethyl)-phenyl)-4-methylsulphonyloxybenzamide
N-(4-(1,1-dimethylethyl)-phenyl)-2-methoxybenzamide
N-(4-(1,1-dimethylethyl)-phenyl)-3-methoxybenzamide
N-(4-(1,1-dimethylethyl)-phenyl)-2-chlorobenzamide
N-(4-(1,1-dimethylethyl)-phenyl)-3-chlorobenzamide
N-(4-(1,1-dimethylethyl)-phenyl)-4-chlorobenzamide
N-(4-(1,1-dimethylethyl)-phenyl)-4-methylthiobenzamide
N-(4-(1,1-dimethylethyl)-phenyl)-4-methylbenzamide
N-(4-(1,1-dimethylethyl)-phenyl)-4-cyanobenzamide
N-(4-(1,1-dimethylethyl)-phenyl)-4-nitrobenzamide
N-(4-(1,1-dimethylethyl)-phenyl)-4-dimethylaminobenzamide
N-(4-(1,1-dimethylethyl)-phenyl)-3,4-dimethoxybenzamide
N-(4-(1,1-dimethylethyl)-phenyl)-3,4-methylenedioxybenzamide
N-(4-(1,1-dimethylethyl)-phenyl)-4-(3-pyridinyloxyben-zamide
N-(4-(1,1-dimethylethyl)-phenyl)-4-aminobenzamide
N-(4-(1-cyanocyclopentyl)-phenyl)-4-methoxybenzamide
N-(4-(1-aminocarbonylcyclopentyl)-phenyl)-4-methoxybenzamide
N-(4-(1-aminomethylcyclopentyl)-phenyl)-4-methoxybenzamide.

The following Examples are given for the purpose of illustrating the present invention:

EXAMPLE 1

4-(1,1-Dimethylethyl)-N-(4-methoxyphenyl)-benzamide

To a solution of 2.50 g. (0.02 mol) 4-methoxyaniline and 3 ml. (0.22 mol) triethylamine in 30 ml. dichloromethane is added dropwise with ice cooling and the exclusion of moisture within the course of 1 hour a solution of 4.3 ml. (0.22 mol) 4-(1,1-dimethylethyl)benzoic acid chloride in 40 ml. dichloromethane. After stirring for 30 minutes at ambient temperature, the solvent is removed in a vacuum and the residue is digested with water and filtered off with suction. There are obtained 4.2 g. of crude product which is recrystallised from 150 ml. ethyl acetate and dried in a vacuum at 40° C. Yield 3.0 g. (53% of theory) of colourless crystals, m.p. 119°–120° C.

Analogously to Example 1, by the reaction of the given amines with 4-(1,1-dimethylethyl)-benzoic acid chloride, there are obtained the following compounds:

| | designation | yield % | m. p. °C. | recryst. from |
|---|---|---|---|---|
| 2 | 4-(1,1-dimethylethyl)-N-(4-hydroxyphenyl)-benzamide from 4-hydroxyaniline | 70 | 197–201 | toluene |
| 3 | 4-(1,1-dimethylethyl)-N-(4-propyloxyphenyl)-benzamide from 4-propoxyaniline | 62 | 130–132 | ligroin |
| 4 | N-(4-allyloxyphenyl)-4-(1,1-dimethylethyl)-benzamide from 4-allyloxyaniline | 44 | 115–117 | ethanol |
| 5 | N-(4-benzyloxyphenyl)-4-(1,1-dimethylethyl)-benzamide from 4-benzyloxyaniline | 75 | 178–180 | toluene |
| 6 | 4-(1,1-dimethylethyl)-N-(4-methylsulphonyloxyphenyl)-benzamide from 4-methylsulphonyloxyaniline | | | |
| 7 | 4-(1,1-dimethylethyl)-N-(2-methoxyphenyl)-benzamide from 2-methoxyaniline | 45 | oil | |
| 8 | 4-(1,1-dimethylethyl)-N-(3-methoxyphenyl)-benzamide from methoxyaniline | 57 | 105–106 | ethanol |
| 9 | N-(2-chlorophenyl)-4-(1,1-dimethylethyl)-benzamide from 2-chloroaniline | 53 | 65–66 | ligroin |
| 10 | N-(3-chlorophenyl)-4-(1,1-dimethylethyl)-benzamide from 3-chloroaniline | 87 | 105–107 | ligroin |
| 11 | N-(4-chlorophenyl)-4-(1,1-dimethylethyl)-benzamide from 4-chloroaniline | 82 | 198–201 | ethanol |
| 12 | 4-(1,1-dimethylethyl)-N-(4-methylthiophenyl)-benzamide from 4-methylthioaniline | 60 | 119–121 | toluene |
| 13 | 4-(1,1-dimethylethyl)-N-(4-methylphenyl)-benzamide from 4-methylaniline | 70 | 123–125 | ligroin |
| 14 | N-(4-cyanophenyl)-4-(1,1-dimethylethyl)-benzamide from 4-cyanoaniline | 70 | 188–190 | ethanol |
| 15 | 4-(1,1-dimethylethyl)-N-(4-nitrophenyl)-benzamide from 4-nitroaniline | 68 | 158–159 | ethanol |
| 16 | N-(4-dimethylaminophenyl)-4-(1,1-dimethylethyl)-benzamide from 2-methoxyaniline | 49 | 148–150 | isohexane |
| 17 | N-(3,4-dimethoxyphenyl)-4-(1,1-dimethylethyl)-benzamide from 3,4-dimethoxyaniline | 55 | 266–268 | ethanol |
| 18 | 4-(1,1-dimethylethyl)-N-(3,4-methylenedioxyphenyl)-benzamide from 2,4-methyleneaniline | 72 | 128–129 | ligroin |
| 19 | 4-(1,1-dimethylethyl)-N-(4-(3-pyridinyloxy)-phenyl)-benzamide from 4-(3-pyridinyloxy)-aniline | 63 | 145 | toluene/ ligroin |

EXAMPLE 20

N-(4-Aminophenyl)-4-(1,1-dimethylethyl)-benzamide 4.5 g. (0.015 mol) 4-(1,1-Dimethylethyl)-N-(4-nitrophenyl)-benzamide (Example 15 ) are hydrogenated at normal pressure and ambient temperature in the presence of 0.5 g. 10% palladium on charcoal. After 30 minutes, the reaction mixture is filtered and the filtrate is evaporated in a vacuum. The residue is digested with ligroin and filtered off with suction. There are obtained 3.4 g. (85% of theory) of the title compound; m.p. 111°–113° C.

Example 21

N-(4-Methoxyphenyl)-4-(1-cyanoethyl)-benzamide

Analogously to Example 1, 0.17 g. 4-methoxyaniline is reacted with 0.3 g. 4-(1-cyanoethyl)-benzoic acid chloride to give, after recrystallisation from methanol, 0.23 g. (60% of theory) of the title compound in the form of a cream-coloured powder; m.p. 176°–178° C.

The 4-(1-cyanoethyl)-benzoic acid chloride used as starting material is prepared as follows:

1.75 g. (10 mMol) Methyl 4-(cyanomethyl)-benzoate (see J. F. Codington et al., J. Org. Chem., 17, 1035/1952) and 0.28 g. tetrabutylammonium bromide in 9.7 ml. 50% aqueous sodium hydroxide solution are mixed, while cooling with ice, with 0.62 ml. iodomethane, after 1 hour dichloromethane and water are added thereto, the dichloromethane is separated off, washed neutral with water, dried and the solvent is removed in a vacuum. The oil remaining behind is purified by column chromatography (silica gel, n-heptane/methyl ethyl ketone 6:1 v/v). The appropriate fractions are combined and the solvent is removed in a vacuum. There is obtained 0.57 g. (30% of theory) methyl 4-(1-cyanoethyl)-benzoate in the form of an oil.

This ester is stirred for 4 hours in 5 ml. methanol and 1.7 ml. 2N aqueous sodium hydroxide solution, the solvent is removed in a vacuum, the residue is acidified with 2N hydrochloric acid and the precipitate is filtered off with suction, washed with water and dried. There is obtained 0.32 g. (69% of theory) 4-(1-cyanoethyl)-benzoic acid; m.p. 113°–116° C.

This acid is heated with 0.37 ml. thionyl chloride to 80° C. After 15 minutes, the thionyl chloride is removed in a vacuum to give 0.3 g. (90% of theory) 4-(1-cyanoethyl)-benzoic acid chloride in the form of an oil which is immediately reacted without further purification.

Example 22

N-(4-Methoxyphenyl)-4-(1-cyano-1-methylethyl)-benzamide

Analogously to Example 1, by the reaction of 1 g. 4-methoxyaniline with 1.86 g. 4-(1-cyano-1-methylethyl)benzoic acid chloride, there is obtained 1.64 g. (69% of theory) of the title compound in the form of a cream-coloured powder; m.p. 164°–168° C. after recrystallisation from methanol.

The 4-(1-cyano-1-methylethyl)-benzoic acid chloride used as starting material is prepared as follows:

0.9 g. Methyl 4-(cyanomethyl)-benzoate (J. F. Codington et al., J. Org. Chem., 17, 1035/1952) and 0.15 g. tetrabutylammonium bromide in 5 ml. 50% aqueous sodium hydroxide solution is mixed, while cooling with ice, with 1 ml. iodomethane. The reaction mixture is stirred for 16 hours at ambient temperature and then worked up as described in Example 21. There is obtained 1 g. (96% of theory) methyl 4-(1-cyano-1-methylethyl)-benzoate; m.p. 45°–50° C.

0.5 g. of this ester is saponified as described in Example 21 to give 0.35 g. (76% of theory) 4-(1-cyano-1-methylethyl)-benzoic acid; m.p. 172°–178° C.

This acid is reacted with thionyl chloride as described in Example 21 to give 4-(1-cyano-1-methylethyl)-benzoic acid chloride in the form of an oil which is used without further purification.

Example 23

N-(4-Methoxyphenyl)-4-(1-aminocarbonyl)-1-methylethyl)-benzamide 1 g. N-(4-Methoxyphenyl)-4-(1-cyano-1-methylethyl)-benzamide (Example 22) in 6 ml. dichloromethane is mixed, while cooling with ice and with vigorous stirring, with 1.59 ml. hydrogen peroxide (30%), 0.23 g. tetrabutylammonium hydrogen sulphate and 1.27 ml. 2% aqueous sodium hydroxide solution. The reaction mixture is stirred for 8 hours at ambient temperature, the organic phase is separated off, the solvent is evaporated in a vacuum and the crystalline residue is purified by column chromatography (silica gel; n-heptane/methyl ethyl ketone 1:1 v/v). The appropriate fractions are evaporated in a vacuum to give 0.16 g. (15% of theory) of the title compound; m.p. 176°–180° C.

EXAMPLE 24

N-(4-(1,1-Dimethylethyl)-phenyl)-4-methoxycinnamic acid amide

Under the reaction conditions of Example 1, 2.5 g. 4-(1,1-dimethylethyl)-aniline are reacted with 2.5 g. 4-methoxycinnamic acid chloride to give 1.0 g. of the title compound; m.p. 158°–160° C.

EXAMPLE 25

4-(1,1-Dimethylethyl)-N-(4-methoxy-2-nitrophenyl)-benzamide

To 16.8 g. (0.1 mol) 4-methoxy-2-nitroaniline in 150 ml. anhydrous pyridine are added dropwise, while cooling with ice, 19.7 g. (0.1 mol) 4-tert.-butylbenzoic acid chloride. The reaction mixture is stirred for 1 hour at ambient temperature, poured into 1 liter of cold water and the precipitate obtained is filtered off with suction. There are obtained 32.3 g. (98% of theory) of the title compound in the form of yellow crystals; m.p. 103°–107° C.

EXAMPLE 26

4-(2-Amino-1,1-dimethylethyl)-N-(4-methoxyphenyl)-benzamide 2 g. 4-(1-Cyano-1-methylethyl)-N-(4-methoxyphenyl)-benzamide (Example 22) in 100 ml. 10% ethanolic ammonia solution are hydrogenated in the presence of 1 g. 5% rhodium on aluminium oxide for 24 hours at 5 bar. The reaction mixture is filtered with suction, the filtrate is evaporated to dryness and the residue is recrystallised from ethanol. There is obtained 0.68 g. (34% of theory) of the title compound in the form of colourless crystals; m.p. 139°–140° C.

EXAMPLE 27

N-[4-(1-Cyano-1-methylethyl)-phenyl]-4-methoxybenzamide

Analogously to Example 25, 4-(1-cyano-1-methylethyl)-aniline is reacted with 4-methoxybenzoic acid chloride to give a yield of 85% of theory of the title compound in the form of beige crystals; m.p. 169°–171° C. A sample thereof is recrystallised from ethanol and then has a melting point of 172°–174° C.

EXAMPLE 28

N-[4-(1-Aminocarbonyl-1-methylethyl)-phenyl]-4-methoxybenzamide 5 g. N-[4-(1-Cyano-1-methylethyl)-phenyl]-4-methoxybenzamide (Example 27) are stirred for 20 hours at ambient temperature in 100 ml. concentrated sulphuric acid, poured on to ice, the precipitate is filtered off with suction, dissolved in hot glacial acetic acid, water added thereto until the commencement of turbidity and then left to cool. There are obtained 2.2 g. (42% of theory) of the title compound in the form of colourless crystals; m.p. 234°–235° C.

EXAMPLE 29

N-[4-(2-Amino-1,1-dimethylethyl)-phenyl]-4-methoxybenzamide 5 g. N-[4-(1-Cyano-1-methylethyl)-phenyl]-4-methoxybenzamide (Example 27) are hydrogenated at 90° C. and 120 bar hydrogen pressure in 40 ml. ethanol in the presence of 40 ml. liquid ammonia and 2 g. Raney nickel. The reaction mixture is filtered and the filtrate evaporated to dryness in a vacuum. After column chromatographic purification (400 ml. silica gel 60; dichloromethane/methanolic ammonia 30:1 v/v), there are obtained 2.6 g. of colourless crystals which are heated in 100 ml. 1M hydrochloric acid. After cooling, there are obtained 2.3 g. (40% of theory) of the title compound as hydrochloride in the form of colourless leaflets; m.p. 273°-276° C.

EXAMPLE 30

N-[4-(1,1-Dimethylethyl)-phenyl]-4-methoxybenzamide

Analogous to Example 1, from 4-(1,1-dimethylethyl)aniline and 4-methoxybenzoic acid chloride, there is obtained the title compound in a yield of 65% of theory; m.p. 167°-168° C.

EXAMPLE 31

4-(1,1-Dimethylethyl)-N-[4-(ethoxycarbonylmethoxy)-phenyl]-benzamide

To a solution of 0.66 g. sodium in 25 ml. ethanol are added 7 g. 4-(1,1-dimethylethyl)-N-(4-hydroxyphenyl)-benzamide (Example 2) and 3.2 ml. ethyl bromoacetate. The reaction mixture is boiled under reflux for 10 hours, the solvent is removed in a vacuum and the residue is recrystallised from toluene. There are obtained 5.5 g. (60% of theory) of the title compound; m.p. 119°-122° C.

EXAMPLE 32

4-(1,1-Dimethylethyl)-N-[4-(hydroxycarbonylmethoxy)-phenyl]-benzamide 2.0 g. 4-(1,1-Dimethylethyl)-N-[4-(ethoxycarbonylmethoxy)-phenyl]-benzamide (Example 31) are heated in 20 ml. 2N aqueous sodium hydroxide solution, then acidified with concentrated hydrochloric acid, filtered off with suction and washed with water. After recrystallisation from ethyl acetate, there is obtained 1.2 g. (65% of theory) of the title compound; m.p. 179°-181° C.

EXAMPLE 33

4-(1,1-Dimethylethyl)-N-[4-(3-(ethoxycarbonyl)-propoxy)-phenyl]-benzamide

Analogously to Example 31, by the reaction of ethyl 4-bromobutyrate with 4-(1,1-diemthylethyl)-N-(4-hydroxyphenyl)-benzamide (Example 2) there is obtained the title compound in a yield of 56% of theory; m.p. 100°-101° C. after recrystallisation from isopropanol.

EXAMPLE 34

4-(1,1-Dimethylethyl)-N-[4-(3-hydroxycarbonyl)-propoxy)-phenyl]-benzamide

Analogously to Example 32, the compound of Example 33 is saponified to give the title compound in a yield of 67% of theory; m.p. 162°-168° C., after recrystallisation from ethyl acetate.

EXAMPLE 35

4-(1,1-Dimethylethyl)-N-[4-(((N'-cyclohexyl-N'-methylamino)-carbonyl)-propoxy)-phenyl]-benzamide 1.7 g. of the acid obtained in Example 34 and 10 ml. thionyl chloride are boiled under reflux for 1.5 hours. The thionyl chloride is removed in a vacuum and the residue is mixed with 15 ml. dichloromethane and 1 ml. N-cyclohexyl-N-methylamine and stirred for 2 hours at ambient temperature. After shaking with water, the organic phase is evaporated to dryness and the residue purified by column chromatography (dichloeomethane/methanol 98:2 v/v). After evaporation of the desired fractions and recrystallisation of the residue from ethyl acetate, there is obtained 0.5 g. (26% of theory) of the title compound; m.p. 110°-113° C.

EXAMPLE 36

4-(1,1-Dimethylethyl)-N-[4-(hydroxyethoxy)-phenyl]-benzamide 2.2 g. of the compound of Example 31 are reduced with 0.65 g. lithium aluminum hydride in 50 ml. boiling diethyl ether. The reaction mixture is mixed with water, sufficient 10% sulphuric acid is added thereto just to dissolve the precipitate, extracted with diethyl ether, evaporated to dryness and the remaining oil purified by column chromatography (silica gel; dichloromethane/methanol 99:1 v/v). The appropriate fractions are evaporated to dryness in a vacuum, the residue is first recrystallised from ethyl acetate/ligroin (1:1 v/v) and then from toluene to give 0.6 g. (31% of theory) of the title compound; m.p. 136°-142° C.

EXAMPLE 37

4-(1,1-Dimethylethyl)-N-[(4-methoxyphenyl)-methyl]-benzamide

Analogously to Example 1, from 4-(1,1-dimethylethyl)-benzoic acid chloride and 4-(methoxyphenyl)methylamine is obtained the title compound in a yield of 71% of theory; m.p. 145°-148° C., after recrystallisation from isohexane.

EXAMPLE 38

4-(1,1-Dimethylethyl)-N-[2-(nitro-4-(3-pyridinyloxy)-phenyl]-benzamide

To 2.35 g. 4-(1,1-dimethylethyl)-N-[4-(3-pyridinyloxy)-phenyl]-benzamide in 60 ml. acetic anhydride are added dropwise, within the course of 2 hours, 2.7 ml. 100% nitric acid (d=1.52), then poured on to ice, extracted with dichloromethane, the solvent removed in a vacuum and the residue recrystallised from toluene/ligroin. There is obtained 0.82 g. (31% of theory) of the title compound; m.p. 103° C.

EXAMPLE 39

4-(1-Cyanocyclopentyl)-N-(4-methoxyphenyl)-benzamide a) To 22.3 g. (127 mMol) methyl 4-(cyanomethyl)-benzoate (J. F. Codington, E. Mosttig, J. Org. Chem., 17, 1032/1952) and 1.1 g. benzyltributylammonium bromide in 87 ml. concentrated aqueous sodium hydroxide solution are rapidly added dropwise 16.5 ml. (140 mMol) 1,4-dibromobutane. The temperature increases to 70° C. The reaction mixture is stirred for 2 hours, during which time it cools to ambient temperature. 500 ml. Ice-water are added thereto and extracted with dichloromethane. The organic phase is extracted with water, dried over anhydrous sodium sulphate, filtered and the filtrate evaporated to dryness. The residue is filtered with dichloromethane through a column of silica gel "60" (length 50 cm., diameter 5 cm.). After removal of the solvent, there are obtained 21 g. (72% of theory) methyl 4-(1-cyanocyclopentyl)-benzoate; m.p. 32°-33° C.

b) 19.4 g. (85 mMol) Methyl 4-(1-cyanocyclopentyl)-benzoate are kept for 20 hours at ambient temperature in 180 ml. methanol and 60 ml. 2N aqueous sodium hydroxide solution. The solvent is removed in a vacuum, the residue is acidified with 6N hydrochloric acid, filtered and the filtrate washed with water. There are obtained 18 g. 4-(1-cyanocyclopentyl)-benzoic acid. Yield 98% of theory; m.p. 170°-174° C.

c) 5.8 g. (27 mMol) 4-(1-cyanocyclopentyl)-benzoic acid are reacted with thionyl chloride and subsequently with 4-methoxyaniline as described in Example 1 to give 5.1 g. of the title compound; m.p. 163°-168° C.

EXAMPLE 40

4-(1,1-Dimethylethyl)-N-[4-(2-hydroxyethoxy)-phenyl]-benzamide 2.2 g. (6.2 mMol) of the compound prepared in Example 31 in 50 ml. dry diethyl ether are heated with 1 g. lithium aluminium hydride, subsequently poured into water and a little 10% sulphuric acid, extracted with diethyl ether, dried over anhydrous sodium sulphate, filtered and the solvent removed in a vacuum. The residue is then recrystallised from toluene to give the title compound in a yield of 25% of theory; m.p. 136°-142° C.

PHARMACOLOGICAL TEST RESULTS

Erythrocyte aggregation was determined with a minierythrocyte aggregometer of the firm Myrenne, Rötgen (see Kiesewetter et al., Biomed. Technik, 27, 209-213/1982). This apparatus produces as the test result a dimensionless index which increases with increasing aggregation tendency of the tested compound.

The investigations were carried out with human blood from healthy donors. The blood was adjusted to a haematocrit of 45% and incubated with a control solution or with a solution of a test substance. The erythrocyte aggregation was then measured. Each compound was investigated at a concentration of $10^{-5}$ molar. Two investigations with the blood from two donors were conducted for each compound. The difference of the aggregation indices ($\Delta E$) between the initial value of the control solution and the values with the solutions of the test compounds was calculated.

In the following Table, the findings obtained for the erythrocyte aggregation ($\Delta E$), are set forth. The lower a given value of ($\Delta E$), the more effective is the test compound. In comparison, venoruton, a mixture of various O-($\beta$-hydroxyethyl)-rutosides, at a comparable concentration of $1.7 \times 10^{-5}$M, only brings about a change of the erythrocyte aggregation index of 0.4. Even at a concentration of $1.7 \times 10^{-3}$M, the change produced by venoruton, which is reported to inhibit the tendency towards erythrocyte aggregation (see Schmid-Schönbeim et al., VASA, 4, 263-270/1975), only amounts to $-3.9 \pm 0.9$.

In comparison with the prior art, the compounds of the present invention clearly more strongly inhibit erythrocyte aggregation.

TABLE

| Inhibition of the erythrocyte aggregation ($\Delta E$) | |
|---|---|
| Compound of Example | $\Delta E$ |
| 1 | −11.1 |
| 3 | −7.2 |
| 4 | −10.0 |
| 8 | −9.7 |
| 14 | −8.0 |
| 16 | −10.4 |
| 17 | −11.0 |
| 18 | −9.2 |

We claim:

1. A pharmaceutical composition for inhibiting the aggregation of erythrocytes or thrombocytes comprising an inhibiting amount of at least one compound of the formula:

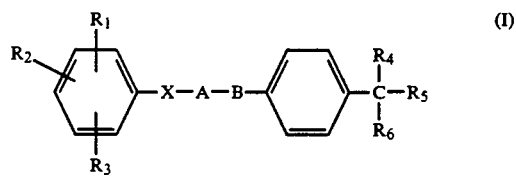

wherein $R_1$, $R_2$ and $R_3$ are the same or different and each represents a hydrogen atom, $C_1$-$C_6$-alkyl, $C_2$-$C_6$-alkenyl, $C_3$-$C_7$-cycloalkyl, halogen, nitro, amino, hydroxyl or cyano, or a hydroxyl group substituted by $C_1$-$C_6$-alkyl, $C_2$-$C_6$-alkenyl, $C_1$-$C_6$-alkylsulphonyl, hydroxy-$C_1$-$C_6$-alkyl, carboxy-$C_1$-$C_6$-alkyl, or $C_1$-$C_6$-alkoxycarbonyl-$C_1$-$C_6$-alkyl or or an amino group substituted at least once by $C_1$-$C_6$-alkyl, or a $C_1$-$C_6$-alkylthio group X is a valency bond or a $C_1$-$C_6$-alkylene radical, A is imino —NH—, B is carbonyl, $R_4$ is methyl or cyano, $R_5$ is a hydrogen atom or a $C_1$-$C_6$-alkyl radical and $R_6$ is a $C_1$-$C_6$-alkyl or $C_3$-$C_7$-cycloalkyl radical, or $R_5$ and $R_6$, together with the carbon atom to which they are attached, represent a $C_3$-$C_7$-cycloalkyl ring, the optically-active forms thereof, the tautomers thereof and the physiologically acceptable salts thereof, and a pharmaceutically acceptable carrier.

2. The composition of claim 1, wherein $R_1$ is a hydrogen atom or nitro, amino, fluoro, chloro, bromo, dimethylamino, diethylamino, cyano, methyl, ethyl, n-propyl, isopropyl, n-butyl, isobutyl, tert-butyl, allyl, hydroxyl, methoxy, ethoxy, propoxy, allyloxy, methylthio, methylsulphonyl, ethoxycarbonylmethoxy, hydroxymethyl, $R_2$ is a hydrogen atom or methyl, ethyl, n-propyl, isopropyl, tert-butyl, chloro, methoxy, hydroxyl or dimethylamino, $R_3$ is a hydrogen atom, a hydroxyl group or a methoxy radical, X is a valency bond or an ethylene radical, $R_4$ is methyl, cyano, $R_5$ is a hydrogen atom or a methyl or ethyl radical and $R_6$ is a methyl, ethyl or cyclopentyl radical, or $R_5$ and $R_6$, together with the carbon atom to which they are attached, form a cyclopentyl radical.

3. The composition of claim 1 or 2, wherein $R_1$ is a substituent in the ortho-position of the phenyl ring and is a hydrogen or chlorine atom, a nitro group or a $C_1$-$C_4$-alkoxy radical.

4. The composition of claim 1 or 2, wherein $R_2$ is a substituent in the meta-position of the phenyl ring and is a hydrogen or chlorine atom or a $C_1$–$C_4$-alkoxy radical.

5. The composition of claim 1 or 2, wherein $R_3$ is a substituent in the para-position of the phenyl ring and is a hydrogen or halogen atom or $C_1$–$C_4$-alkyl, $C_2$–$C_4$-alkenyl, nitro, amino, hydroxyl, cyano, $C_1$–$C_4$-alkoxy, hydroxy-$C_1$–$C_4$-alkoxy, carboxy-$C_1$–$C_4$-alkoxy, $C_1$–$C_4$-alkoxycarbonyl-$C_1$–$C_4$-alkoxy, or di-$C_1$–$C_4$-alkylamino.

6. The composition of claim 1 or 2, wherein $R_4$ is a cyano group or a methyl radical, $R_5$ is a hydrogen atom or a $C_1$–$C_4$-alkyl radical, and $R_6$ is a $C_1$–$C_6$-alkyl radical, or $R_5$ and $R_6$, together with the carbon atom to which they are attached, form a cyclopentyl or cyclohexyl ring.

7. The composition of claim 1, wherein said compound is 4-(1,1-dimethylethyl)-N-(4-methoxyphenyl)-benzamide.

8. The composition of claim 1, wherein said compound is 4-(1,1-dimethylethyl)-N-(4-propyloxyphenyl)-benzamide.

9. The composition of claim 1, wherein said compound is N-(4-allyloxyphenyl)-4-(1,1-dimethylethyl)-benzamide.

10. The composition of claim 1, wherein said compound is 4-(1,1-dimethylethyl)-N-(3-methoxyphenyl)-benzamide.

11. The composition of claim 1, wherein said compound is N-(4-cyanophenyl)-4-(1,1-dimethylethyl)-benzamide.

12. The composition of claim 1, wherein said compound is N-(4-dimethylaminophenyl)-4-(1,1-dimethylethyl)-benzamide.

13. The composition of claim 1, wherein said compound is N-(3,4-dimethoxyphenyl)-4-(1,1-dimethylethyl)-benzamide.

14. The composition of claim 1, wherein said compound is 4-(1,1-dimethylethyl)-N-(3,4-methylenedioxyphenyl)-benzamide.

15. The composition of claim 1, wherein $R_5$ is a hydrogen atom or a $C_1$–$C_6$-alkyl radical selected from the group consisting of methyl, n-propyl, isopropyl, n-butyl, isobutyl, tert.-butyl, pentyl or hexyl.

16. The composition of claim 2, wherein $R_5$ is a hydrogen atom or methyl.

17. The composition of claim 1, wherein $R_1$ is a hydroxy atom or nitro, amino, fluoro, chloro, bromo, dimethylamino, diethylamino, cyano, methyl, ethyl, n-propyl, isopropyl, n-butyl, isobutyl, tert-butyl, allyl, hydroxyl, methoxy, ethoxy, propoxy, allyloxy, methylthio, or ethyoxycarbonylmethoxy; $R_2$ is a hydrogen atom or methyl, ethyl, n-propyl, isopropyl, tert-butyl, chloro, methoxy, hydroxyl or dimethyalmino; and $R_3$ is a hydrogen atom, a hydroxyl group or a methoxy radical.

18. The composition of claim 1, wherein $R_1$, $R_2$ and $R_3$ are the same or different and each represents a hydrogen atom, $C_1$–$C_6$-alkyl, $C_2$–$C_6$-alkenyl, $C_3$–$C_7$-cycloalkyl, halogen, nitro, amino, hydroxyl or a hydroxyl group substituted by $C_1$–$C_6$-alkyl or $C_2$–$C_6$-alkenyl; or an amino group substituted at least once by $C_1$–$C_6$-alkyl.

* * * * *